United States Patent [19]

Jayne et al.

[11] 4,019,991

[45] Apr. 26, 1977

[54] SULPHUR CONTAINING LUBRICATING OIL ADDITIVES

[75] Inventors: Gerald John Joseph Jayne; Herbert Frank Askew, both of Bracknell, England

[73] Assignee: Edwin Cooper & Company Limited, Bracknell, England

[22] Filed: Feb. 27, 1975

[21] Appl. No.: 553,738

[52] U.S. Cl. .................... 252/48.2; 252/47.5; 260/327 M; 260/327 TH; 260/455 B

[51] Int. Cl.² ........................ C10M 1/38

[58] Field of Search ............ 252/47.5, 48.2; 260/327 M, 327 TH, 455 B

[56] References Cited

UNITED STATES PATENTS

| | | | |
|---|---|---|---|
| 2,161,566 | 6/1939 | Fuller | 260/455 B |
| 2,161,584 | 6/1939 | Moran et al. | 260/455 B |
| 2,320,287 | 5/1943 | Lieber et al. | 260/455 B |
| 2,369,150 | 2/1945 | Lincoln et al. | 260/455 B |
| 2,861,913 | 11/1958 | Wegler et al. | 260/455 B |
| 2,865,941 | 12/1958 | D'Amico | 260/455 B |
| 3,644,415 | 2/1972 | Weil et al. | 260/327 TH |
| 3,644,416 | 2/1972 | Weil et al. | 260/327 TH |

*Primary Examiner*—Lewis Gotts
*Assistant Examiner*—D. R. Phillips
*Attorney, Agent, or Firm*—Donald L. Johnson; Robert A. Linn; Joseph D. Odenweller

[57] ABSTRACT

New compounds are derived from intra-molecular and inter-molecular, in the case of a polymer, sulphur bridged hydrocarbon rings containing from 6 to 12 carbon atoms. The hydrocarbon ring is preferably 1,5-cyclooctadiene. The compounds also contain the residue of an alkyl, alkenyl or aralkyl xanthate and may also contain the residue of a further nucleophilic group. The new compounds are useful in lubricating oil compositions. The compositions may also contain other conventional lubricant additives.

27 Claims, No Drawings

SULPHUR CONTAINING LUBRICATING OIL ADDITIVES

The present invention relates to sulphur-containing lubricating oil additives.

According to the present invention there is provided a compound of the formula:

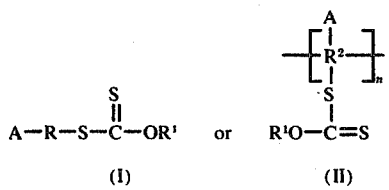

(I)    (II)

wherein in Formula (I) R is the residue of an intramolecular sulphur bridged hydrocarbon ring containing from 6 to 12 carbon atoms or wherein in Formula (II) $-R^2-]_n$ is a polymer comprising the residue of a plurality of substantially intermolecularly sulphur-bridged hydrocarbon rings each containing from 6 to 12 carbon atoms, n being the degree of polymerisation; each $R^1$ is the same or different and is an alkyl or alkenyl group, preferably containing from 1 to 20, more particularly 2 to 8, carbon atoms or an aralkyl group, preferably benzyl or alkylbenzyl; and A is a nucleophilic group.

R and $-[R^2]_n$ are preferably derived from monocyclic olefins such as 1,3,5-cycloheptatriene, cyclooctatetraene, 1,3-cyclooctadiene, 1,5-cyclooctadiene, or 3-alkoxy derivatives thereof and 1,5,9-cyclododecatriene especially the cis-trans-trans version thereof. The sulphur bridging of these hydrocarbons is achieved by reacting with sulphur dichloride or other sulphur chloride compound to yield either monomeric or polymeric derivatives. The sulphur bridges may be oxidised to carry one or two oxygens.

The group A preferably has the formula:

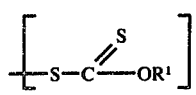

wherein $R^1$ is as defined above and wherein the two groups $R^1$ may be the same or different. Alternatively, the group A may have the formula:

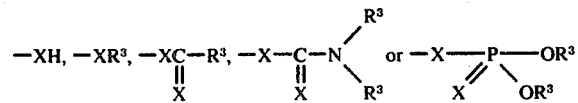

oxygen or sulphur and $R^3$ is an alkyl, aryl, alkaryl or aralkyl group. Further alternatives for A include —CN and —NCS.

The invention also includes a lubricating oil composition which comprises a lubricating oil and a compound as defined above. Such compositions may be intended to be employed directly as lubricants in which case the novel compounds of the present invention will be present in minor amounts, preferably in an amount from 0.01 to 10% by weight, more particularly from 0.5 to 3% by weight, although in a few cases, e.g. 2,6 bis(methoxythiocarbonylthio)-9-thiabicyclo [3,3,1] nonane, oil solubility may be somewhat limited. Thus the number of carbon atoms in the, or each, group $R^1$, and the, or each, group $R^3$ if present, should be sufficiently high to render the compounds oil soluble. On the other hand it is desirable that the number of carbon atoms in the groups $R^1$ and $R^3$ should not be too high since it is believed that the sulphur in the molecule is the active component, otherwise large amounts of the compounds would have to be used to give equivalent sulphur contents. Particularly preferred additives in this respect are compounds in which A is a group of the formula:

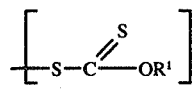

and in which one group $R^1$ is an ethyl or propyl group and the other group is a methyl, ethyl or propyl group.

However, the term lubricating oil composition also embraces the materials known in the art as oil concentrates and additive packages, i.e. concentrated solutions in lubricating oil, optionally together with one or more conventional additives intended to be diluted with further quantities of oil to form the final lubricant. In this case the novel compounds of the present invention may be present in a wide range of proportions e.g. 10% to 90%. In general such concentrated solutions will normally contain from 20% to 50% by weight of the novel compounds of the present invention. The lubricating oil used in the lubricants, or the concentrates or packages, may be any of the well known oils of appropriate viscosity characteristics and may include synthetic oils.

The sulphur-bridged compounds may be prepared by reacting sulphur dichloride with the unsaturated ring compound preferably in an inert solvent at a temperature between −20° and 100° C to give a dichloro derivative. Details of the preparations of these compounds are given in J. Org. Chem. 33, p. 2627 (1968); J. Org. Chem. 31, p. 1679 and 1669 (1966).

The compounds of the present invention may then be prepared by reacting the metal, preferably sodium, or especially potassium, salt of an alkyl, alkenyl or aralkyl xanthate with the dichloro sulphur-bridged compound, in the ratio of two moles of xanthate to one mole of dichloro sulphur-bridged compound when compounds of the formula:

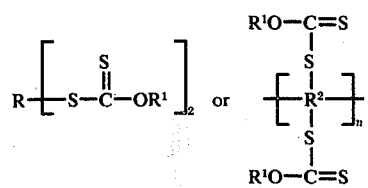

are obtained wherein, R, $R^1$, $R^2$ and n have the same significance as above.

When the xanthate and the dichloro sulphur-bridged compound are reacted in a mole ratio of 1:1. one chlorine remains unreacted. This chlorine atom is then reacted with metal derivatives of the nucleophilic group A.

The invention therefore includes as intermediates compounds having the formulae

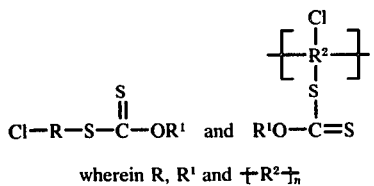

Cl—R—S—$\overset{\text{S}}{\overset{\|}{\text{C}}}$—OR¹ and R¹O—$\overset{\text{S}}{\overset{\|}{\text{C}}}$=S wherein R, R¹ and $(R^2)_n$ have the same significance as above.

Alternatively, the derivative of the nucleophilic group A may be reacted with the dichloro sulphur-bridged compound which may then be reacted with the xanthate.

In some cases, the compounds of the invention may possess residual reactive ethylenically unsaturated double bonds which may be reacted with compounds reactive therewith. Such compounds reacting with residual unsaturation include sulphur, phosphorus pentasulphide, mercaptans, phenols, thiocyanate anions, thiophenols and carboxylic acids. Specific examples of such compounds are mercaptans and carboxylic acids containing from 1 to 16 carbon atoms; phenol (unsubstituted) and thiophenol (unsubstituted). The foregoing compounds may be reacted with the residual unsaturation at a temperature of from 50° to 200° C and in the case of sulphur, thiocyanates and phosphorus pentasulphide no catalyst is required. In the case of the other compounds, however, it may be desirable to use a catalyst known to promote their reaction with ethylenically unsaturated double bonds, such as mineral acids or Lewis acid catalysts such as boron trifluoride or the etherate or phenolate complex thereof.

It will be understood that the lubricating compositions of the present invention may also contain, if desired, conventional lubricant additives such as ancillary antioxidants and antiwear additives (preferably ashless), corrosion inhibitors, dispersants, particularly dispersants of the succinimide type, detergents, thickeners, pour-point depressants and viscosity index improvers. Numerous examples of such conventional additives are described in U.K. patent specification No 1,205,177 and the various documents referred to therein.

There now follows by way of example a description of the preparation of typical compounds in accordance with the present invention:

EXAMPLE 1

Preparation of Intermediate A 2,6-dichloro-9-thiabicyclo[3,3,1]nonane

Methylene chloride (1,250 ml) was stirred at a temperature between 0° and −5° C in a glass vessel fitted with nitrogen inlet and dropping funnels. 1,5 cyclooctadiene (1080 g; 10 moles) and sulphur dichloride (103 g; 10 moles) were added from the dropping funnels at equivalent rates over 5½ hours whilst maintaining the cooling bath at −25° to −30° C. When the addition was complete the mixture was allowed to warm to room temperature overnight and then heated to 46° to 47° C for 2 hours.

The product was precipitated on cooling to below room temperature, filtered off and dried at 50° C in vacuum oven to yield 1511 g (72%) of a product containing 31.9% Cl (calc. 33.7) and 16.4% S (calc. 15.1). The melting point, after recrystallisation, 92.5°–93.5° C, and infrared analysis confirmed that the product was 2,6-dichloro-9-thiabicyclo [3,3,1] nonane.

Preparation of 2,6-bis(butoxythiocarbonylthio—9-thiabicyclo [3,3,1] nonane

Commercial grade potassium hydroxide (66g; 1 mole) of 85% purity was dissolved in n-butanol (300g) by heating rapidly to about 75° C, then cooled rapidly to about 35° C in a water bath. Carbon disulphide (76g; 1.0 moles) was added dropwise over about 50 minutes and the temperature maintained below 40° C by a water bath because of the gentle exotherm, during which time a bright yellow precipitate was formed. When the addition was completed the temperature of the solution of potassium xanthate thus formed was heated to 50° C and a solution of Intermediate A (105.5g; 0.5 moles) in toluene (400 ml) warmed to about 60° C was added.

The mixture increased in viscosity and turned brown and was refluxed (about 91° C) for 4 hours and then cooled to room temperature. After washing three times with 150 ml of water and a further three times with 100 ml of water, the mixture was dried over magnesium sulphate, filtered and stripped on a rotary evaporator to 100° C/20 torr. The residue was filtered through glass-fibre paper on a heated funnel to yield a viscous light brown liquid which solidified to a light yellow solid on standing. 181g (83%) of the product containing 35.8% S (calc. 36.6) and 0.36% Cl was obtained, infrared analysis confirming the structure

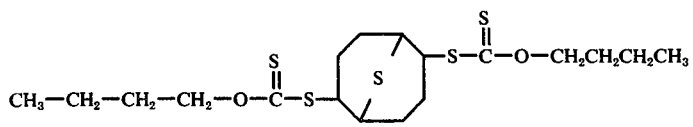

EXAMPLES 2 to 20

Further compounds in accordance with the present invention were prepared in a substantially similar manner to that of Example 1, the details of the preparations and amounts used being summarised in Table 1.

Intermediate B was prepared in a similar manner to Intermediate A, except that the starting materials used were cyclododecatrine (410g; 5 moles) sulphur dichloride (103g; 1.0 moles) and 2.5 liters of methylene dichloride, excess cyclododecatriene than being stripped off and the resulting material recrystallised from petroleum ether (b.pt. 62°–68° C).

Intermediate B¹ was prepared in similar manner to intermediate B, except that 6 moles cyclododecatriene and 1.2 moles sulphur dichloride were used.

Intermediate A¹ was prepared in a similar manner to Intermediate A, except that 1620g 1,5-cyclooctadiene and 1545g sluphur-dichloride were added over about 6½ hours to 1800 ml methylene chloride at 0° C to −5° C.

TABLE 1

| Example No | Name of Product | Intermediate | g. | moles | Alcohol | Amount |
|---|---|---|---|---|---|---|
| 2 | 2,9-bis(butoxythiocarbonylthio)-1 3-thiabicyclo(8,2,1) tridec-5-ene | B | 106 | 0.4 | n-butanol | 300 g |
| 3 | 2,6-bis(methoxythiocarbonylthio)-9-thiabicyclo(3,3,1) nonane | A | 105.5 | 0.5 | methanol | 300 ml |
| 4 | 2,6-bis(benzyloxythiocarbonylthio)-9-thiobicyclo(3,3,1) nonane | A | 105.5 | 0.5 | benzyl | 400 ml |
| 5 | 2,6-bis(ethoxythiocarbonylthio)-9-thiabicyclo(3,3,1) nonane | A | 105.5 | 0.5 | ethanol | 300 ml |
| 6 | 2,6-bis(ethoxythiocarbonylthio)-9-thiabicyclo(3,3,1) nonane | A | 211 | 1.0 | ethanol | 600 ml |
| 7 | 2,6-bis(isopropoxythiocarbonylthio)-9-thiabicyclo(3,3,1) nonane | A | 105.5 | 0.5 | isopropanol | 450 ml |
| 8 | 2,9-bis(isopropoxythiocarbonylthio)-1 3-thiabicyclo(8,2,1) tridec-5-ene | B¹ | 66.3 | 0.25 | isopropanol | 200 ml |
| 9 | 2,9-bis-(2-ethylhexanoxythiocarbonylthio)-1 3-thiabicyclo-(8,2,1)tridec-5-ene | B¹ | 53.0 | 0.2 | 2-ethylhexanol | 300 ml. |
| 10 | 2,9-bis (1-methylbutyoxythiocarbonylthio)-1 3-thiabicyclo (8,2,1) tridec-5-ene | B¹ | 53.0 | 0.2 | pentan-2-ol | 240 ml. |
| 11 | 2,9-bis (benzyloxythiocarbonylthio)-1 3-thiabicyclo (8,2,1) tridec-5-ene | B¹ | 53.0 | 0.2 | benzyl alcohol | 200 ml. |
| 12 | 2,6-bis(n-propoxythiocarbonylthio)-9-thiabicyclo (3,3,1) nonane | A¹ | 211 | 1.0 | n-propanol | 700 ml |
| 13 | 2,6-bis (1-methylpropoxythiocarbonylthio)-9-thiabicyclo (3,3,1) nonane | A¹ | 105.5 | 0.5 | sec-butanol | 400 ml. |
| 14 | 2,6-bis (1-methylbutoxythiocarbonylthio)-9-thiabicyclo (3,3,1) nonane | A¹ | 52.8 | 0.25 | pentan-2-ol | 450 ml. |
| 15 | 2,6-bis (1-ethylpropoxythiocarbonylthio)-9-thiabicyclo (3,3,1) nonane | A¹ | 105.5 | 0.5 | pentan-3-ol | 1100 ml. |
| 16 | 2,6-bis(2-ethylhexanoxythiocarbonylthio)-9-thiabicyclo (3,3,1) nonane | A¹ | 211 | 1.0 | 2-ethylhexanol | 700 ml. |
| 17 | 2,6-bis (tridecanoxythiocarbonylthio)-9-thiabicyclo (3,3,1) nonane | A¹ | 211 | 1.0 | tri-decanol | 1600 ml. |
| 18 | 2,6-bis (allyloxythiocarbonylthio)-9-thiabicyclo (3,3,1) nonane | A¹ | 211 | 1.0 | allyl alcohol | 600 ml. |
| 19 | 2,6-bis (crotyloxythiocarbonylthio)-9-thiabicyclo (3,3,1) nonane | A¹ | 52.75 | 0.25 | crotyl alcohol | 200 ml. |
| 20 | 2,6-bis (cyclohexyloxythiocarbonylthio-9-thiabicyclo (3,3,1) nonane | A¹ | 52.75 | 0.25 | cyclo-hexanol | 350 ml |

| Example No | Weight of KOH (g) | Weight of CS$_2$ (g) | Reflux Time (Hrs) | Reflux Temp. (°C) | Yield g | Yield % | %S Found | %S Calc. | % Cl |
|---|---|---|---|---|---|---|---|---|---|
| 2 | 59.3 | 68.4 | 4 | 90 | 160 | 81.2 | 30.7 | 32.5 | 0.52 |
| 3 | 72.2 | 83.6 | 5¾ | 67 | 124 | 70.4 | 44.9 | 45.2 | 0.74 |
| 4 | 72.2 | 83.6 | 5 | 100 | 221 | 87.4 | 28.5 | 31.7 | 0.3 |
| 5 | 72.2 | 83.6 | 4 | 74 | 157 | 82.3 | 41.3 | 41.9 | 0.47 |
| 6 | 144.4 | 167.2 | 4 | 74 | 303 | 79.2 | 40.0 | 41.9 | 0.5 |
| 7 | 72.2 | 84 | 4 | 74 | 188 | 92.0 | 34.0 | 39.0 | 0.5 |
| 8 | 39.5 | 45.6 | 3 | 78 | 94.1 | 81.2 | 30.08 | 34.5 | 0.28 |
| 9 | 20.0+ | 38.0 | 3 | 80 | 96.4 | 79.7 | 24.97 | 26.5 | 0.29 |
| 10 | 32.9 | 38.0 | 3 | 80 | 89.5 | 86.1 | 27.2 | 30.8 | 0.75 |
| 11 | 32.9 | 38.0 | 3 | 80 | 90.0 | 84.6 | 27.8 | 30.1 | 0.60 |
| 12 | 144.4 | 167.2 | 3 | 85 | 342.7 | 83.6 | 38.5 | 39.0 | 0.56 |
| 13 | 72.2 | 84.0 | 3 | 70–80 | 201.9 | 92.2 | 34.2 | 36.6 | 0.36 |
| 14 | 49.5 | 57.0 | 3½ | 90 | 111.0 | 95.2 | 32.4 | 34.4 | 0.33 |
| 15 | 72.2 | 84.0 | 2 | 80 | 183.7 | 78.8 | 32.9 | 34.4 | 0.49 |
| 16 | 144.4 | 167.2 | 4 | 82–85 | 495.3 | 90.0 | 28.1 | 29.1 | 0.46 |
| 17 | 158 | 183 | 4 | 90 | 628.2 | 91.0 | 23.15 | 23.2 | 0.14 |
| 18 | 145 | 167 | 3 | 80 | 362.5 | 89.3 | 38.1 | 39.5 | 0.64 |
| 19 | 39.5 | 45.6 | 3 | 55–60 | 104.7 | 96.5 | 36.2 | 36.87 | 0.26 |
| 20 | 39.5 | 45.6 | 3 | 80 | 88.0 | 71.8 | 31.63 | 32.65 | 0.27 |

+Na OH used instead of KOH

EXAMPLE 21

Preparation of Intermediate 2,6-dichloro - 9 - thiabicyclo (3,3,1) nonane

Sulphur dichloride (1030g. 10 m.) and 1,5-cyclooctadiene (1080g. 10 m.) were added simultaneously at equal molar rates, to methylene dichloride (1250 ml.) maintained at 0° to −5° C. over a period of 4½ hours. The resulting mixture was allowed to warm to room temperature overnight, then heated to 45° C. for 2 hours, cooled to room temperature and refrigerated to yield 1670.6g (79.3%) of solid product which was filtered off and dried in a vacuum oven at 50° C.

Analysis of product:- %S 14.86 (calc. 15.1); %Cl.31.7 (calc. 33.7).

Preparation of 2,6-bis (methoxy/ethoxythiocarbonylthio)-9-thiabicyclo (3,3,1) nonane Potassium hydroxide (72.2g. of 1.1 m. of 85% purity) was added to a mixture of alcohols (ethanol 177g + methanol 123g.) and heated until dissolved. The resulting mixture was cooled to about 40° C and carbon disulphide (84g. 1.1 m.) added while maintaining the reaction temperature at about 40° C., whereafter a solution of the intermediate prepared above (105.5g 0.5m. dissolved in 400 ml. toluene) was added over a period of 40 minutes during which the temperature was maintained in the range 40°–50° C. A yellow precipitate formed. The reaction mixture was refluxed (72° C.) for 4 hours, then washed with water after addition of toluene to ensure phase separation and the organic layer separated. The organic layer was filtered, dried over anhydrous magnesium sulphate overnight, refiltered, stripped to 100° C./20 torr and the residue refiltered to yield 106g. (57,6%) of the product as a viscous red liquid.

Analysis of product:- 44.7%S (calc. 43.5%); 0.65%Cl. (calc. 0).

EXAMPLE 22

2,6 -bis (methoxy/n - butoxythiocarbonylthio)-9-thiabicyclo (3,3,1) nonane

The intermediate was prepared in similar manner to Example 21 from 940 ml. methylene dichloride, 774g. (7.5 m.) sulphur dichloride and 810g. (7.5 m.) 1,5-cyclooctadiene Analysis 16.4%S (calc. 15.1): 33.5%Cl. (calc. 33.7).

The product was prepared in similar manner to Example 21 from 36.1g. 85% purity potassium hydroxide, a mixture of 61.6g methanol and 142.5g. n-butanol, 42g. (0.55 m.) carbon disulphide and 52.7g. (0.25 m.) of intermediate dissolved in 200 ml. toluene; and the yield was 59.7g.

Analysis of product: 39.2%S (calc. 40.4%); 0.6%Cl. (calc. 0).

EXAMPLE 23

The same product as in Example 22 was prepared in similar manner except in that the mixture of alcohols consisted of 31.4g methanol and 212g. n-butanol; and the yield was 80.1g.

Analysis of product: 39.4%S (calc. 38.3%) 0.33%Cl. (calc. 0)

EXAMPLE 24

2 - allyloxythiocarbonylthio - 6 - isopropyloxythiocarbonylthio - 9 - thiabicyclo (3,3,1) nonane The product was prepared in similar manner to Example 21 from potassium hydroxide (72.5g. 1.1 m. 85% purity), a mixture of allyl alcohol (145g. 2.5m.) isopropyl alcohol (150g. 2.5 m.), carbon disulphide (83.6g. 1.1 m.) and 2,6dichloro-9-thiabicyclo (3,3,1) nonane (105.5g. 0.5 m.) in 400 ml. toluene; and the yield was 150g. (73.5%).

Analysis of product: 37.5%S (calc. 39.2); 0.35%Cl. (calc. 0.00).

EXAMPLE 25

2,6 bis (methoxy/ethoxythiocarbonylthio) - 9 -thiabicyclo (3,3,1) nonane a. Potassium hydroxide (36.1g. 0.55 m. 85% purity) was dissolved in ethanol (150 ml. 740P) by heating to 50° C. for 10 minutes. The solution was cooled to 40° C. and carbon disulphide (41.8g. 0.55 m.) added over 20 minutes, toluene (50 ml.) being added to maintain stirring. A solution of 2,6-dichloro - 9 - thiabicyclo (3,3,1) nonane (105.5g. 0.5 m.) in toluene (400 ml.) was added over 40 minutes with cooling. The temperature was allowed to rise under the exotherm until a steady temperature was reached and the mixture then heated to 70° C. for 4 hours. The product was allowed to cool and was filtered, two phases being present. After drying over magnesium sulphate and filtration the solvent was stripped off to yield product (a).

b. Potassium hydroxide (36.1g. 1.1 m. 85% purity) was dissolved in methanol (150 ml.) in a fresh glass vessel. Carbon disulphide (41.8g. 0.55 m.) was added over ½ hour with stirring. Product (a) dissolved in toluene (400 ml.) was added over 3/4 hour and the mixture heated for 4 hours at 64° C. After cooling the product was washed with three portions of water, toluene being added to aid separation. After drying over magnesium sulphate, filtering and stripping 150g. (81.5%) of the above named product, a viscous orange liquid, was obtained.

Analysis of product: 35.6%S (calc. 43.5%); 0.75%Cl. (calc. 0.00%).

Three further examples (Examples 26 to 28) were carried out in substantially the same manner as in Example 25, details only of the reactants and product analyses therefore being specified in each case.

EXAMPLE 26

2,6 bis (methoxy/butoxythiocarbonylthio) - 9 - thiabicyclo (3,3,1) nonane a. KOH (72.2g. 1.1 m. 85% purity), n-butanol (400 ml.), $CS_2$ (83.6g. 1.1 m.) 2.6-dichloro-9-thiabicyclo (3,3,1) nonane (211g. 1 m.) and toluene (800 ml.).

b. KOH (72.2g. 1.1 m. 85% purity), methanol (300 ml.), $CS_2$ (83.6g. 1.1 m.) and toluene (600 ml.). Reaction product of (a) added to (b). Yield of final product was 332.8g. (84%).

Analysis of product (orange liquid): 31.7%S (calc. 40.4); 0.55%Cl. (calc. 0.00).

EXAMPLE 27

2,6 bis(ethoxy/butoxythiocarbonylthio) -9 - thiabicyclo (3,3,1) nonane a. KOH (18g. 0.275 m. 85% purity) n-butanol (100 ml.) $CS_2$ (21g. 0.275 m.) 2, 6 dichloro- 9 thia bicyclo (3,3,1) nonane (52.8g. 0.25 m.) toluene (200 ml.).

b. KOH (18g. 0.275 m. 85% purity) ethanol (100 ml.) $CS_2$ (21g. 0.275 m.) toluene (200 ml.) Reaction product of (a) added to reaction product of (b). Yield of final product was 72.6g. (71%).

Analysis of product: 31.4%S (calc. 39%) 0.5%Cl. (calc. 0.00)

EXAMPLE 28

2 - allyloxythiocarbonuylthio - 6 - isopropoxythiocarbonylthio - 9 - thiabicyclo (3,3,1) nonane a. KOH (32.9g. 0.5 m. 85% purity), iso propyl alcohol (200 ml.) $CS_2$ (38g. 0.5 m.) 2,6 - dichloro - 9 - thia bicyclo (3,3,1) nonane (105.5g. 0.5 m.) toluene (400 ml.)

b. KOH (39.5g. 0.6 m. 85% purity) allyl alcohol (105 ml.) $CS_2$ (45.6g. 0.6 m.). Reaction product of (a) added to reaction product (b). Yield of final product was 176.4g. (86.5%).

Analysis of product: 34.02%S (calc. 39.2%); 0.41%Cl. (calc. 0.00%).

EXAMPLE 29

2-Dodecylthio-6-isopropoxythiocarbonylthio-9-thiabicyclo (3,3,1) nonane n-Dodecylmercaptan (50.5g. 0.25 m.) was dissolved by stirring in toluene (200 ml.) and then sodium metal (5.8g. 0.25 m.) added over 20 minutes at 100° C. After heating for 2 hours at 110° C. a white suspension was obtained which was added to a solution of 2,6-dichloro-9-thia bicyclo (3,3,1) nonane (211g. 0.25 m.) in toluene (200 ml.) over 5 minutes and subsequently heated to 100° C. for 3 hours, cooled and filtered through glass-fibre filter and added to a solution of potassium isopropyl xanthate in isopropyl alcohol.

The latter was prepared by dissolving potassium hydroxide (20g. 0.3 m. 85% purity) in isopropyl alcohol and adding carbon disulphide (22.8g. 0.3 m.) thereto whilst maintaining the temperature at 38°–40° C. The mixture was heated at 80° C. for 3 hours, cooled, washed with water and dried over magnesium sulphate to yield 101.4g. (85.2%) of the desired product.

Analysis of product: 26.1%S (calc. 26.9%); 0.68%Cl. (calc. 0.00%).

EXAMPLES 30 TO 37

Further compounds in accordance with the present invention were prepared in a substantially similar manner to that of Example 29, details of the reactants and product analyses being summarised in Table 2 in which, for convenience, 2,6-dichloro-9-thiabicyclo (3,3,1) nonane has been abbreviated to 2,6 DTN.

TABLE 2

| Example No | Name of Product | NUCLEOPHILE SOURCE | Wt (g) | NAME | WT (g) | TOLUENE (ml.) |
|---|---|---|---|---|---|---|
| 30 | 2-(diisobutyl)dithiophosphato-6-isopropoxythiocarbonylthio-9-thiabicyclo (3,3,1) nonane | diisobutyl dithio-phosphoric acid | 67 | Et₃N | 25.3 | 100 |
| 31 | 2-(N,N-dibutyl thiocarbamyl thio)-6-(isopropoxythiocarbonylthio)-9-thiabicyclo(3,3,1)nonane | N,N-dibutyl thiocarbamate | ++++ | ++++ | ++++ | ++++ |
| 32 | 2-(butoxythiocarbonylthio)-6-phenoxy-9-thiabicyclo (3,3,1) nonane | phenol | 47g | Na metal | 11.5 | 1200 |
| 33 | 2-(butoxythiocarbonylthio)-6-(o-t-butyl-p-methylphenoxy)-9-thiabicyclo (3,3,1)nonane | t butyl-p-cresol | 82g | Na metal | 11.5 | 800 |

| Example No | 2,6 DTN wt (g) | TOLUENE ml. | KOH WT (g) | ALCOHOL NAME | AMOUNT ml. | CS₂ wt(g) | %S FOUND | %S CALC | %Cl Calc (0.00) | OTHER ELEMENTS ELEMENTS | FOUND | CALC |
|---|---|---|---|---|---|---|---|---|---|---|---|---|
| 30 | 52.8 | 200 | 19.8 | isopropanol | 150 | 22.8 | 32.1 | 31.0 | 0.23 | P | 5.86 | 6.0 |
| 31 | 52.8 | " | 19.8 | " | " | " | 28.8 | 33.4 | 0.26 | N | 3.27 | 2.92 |
| 32 | 105.5 | 400 | 33.0 | n-butanol | 200 | 38 | 23.4 | 25.1 | 0.39 | — | — | — |
| 33 | 105.5 | 400 | 33.0 | n-butanol | 200 | 38 | 21.4 | 21.2 | 0.22 | — | — | — |

| Example No | Name of product | NUCLEOPHILE SOURCE | Wt (g) | ALKALI NAME | WT (g) | TOLUENE (ml.) |
|---|---|---|---|---|---|---|
| 34 | 2-(isopropoxythiocarbonylthio)-6-(o-t-butyl-p-methylphenoxy)-9-thiabicyclo(3,3,1)nonane | t-butyl-p-cresol | 164 | Na metal | 23 | 1500 |
| 35 | 2-(butoxythiocarbonylthio)-6-(2,6-di-t-butyl-p-methylphenoxy)-9-thiabicyclo (3,3,1) nonane | 2,6-di-t-butyl p-cresol | 110 | Na metal | 11.5 | 800 |
| 36 | 2-(octanoxythiocarbonylthio)-6-isothiocyanato-9-thiabicyclo (3,3,1)nonane | isothiocyanate | | potassium salt | 48.5 | 1000++ |
| 37 | 2-(hexanoxythiocarbonylthio)-6-isothiocyanato-9-thiabicyclo (3,3,1)nonane | isothiocyanate | | potassium salt | 48.5 | 1000++ |

| EXAMPLE No. | 2,6 DTN wt (g) | TOLUENE ml. | KOH WT (g) | ALCOHOL NAME | AMOUNT ml. | CS₂wt(g) | %S FOUND | %S CALC | %Cl Calc (0.00) | OTHER ELEMENTS ELEMENT | FOUND % | CALC |
|---|---|---|---|---|---|---|---|---|---|---|---|---|
| 34 | 211 | 800 | 72.2 | iso-propyl | 400 | 83.6 | 21.1 | 21.86 | 0.38 | — | — | — |
| 35 | 105.5 | 400 | 36.1 | n-butanol | 200 | 42 | 18.5 | 18.9 | 0.42 | — | — | — |
| 36 | 105.5 | 500 | 52.6 | n-octanol | 450 | 60.8 | 28.5 | 31.8 | 0.40 | N | 2.18 | 3.4 |
| 37 | 105.5 | 500 | 52.6 | n-hexanol | 400 | 60.8 | 31.8 | 34.2 | 0.39 | N | 2.50 | 3.7 |

++Methyl ethyl ketone used as solvent
++++Sodium N. N dibutyl dithio carbamate was prepared by dissolving NaOH (10g 0.25m.) in a mixture of water (15ml.) and ethanol (40ml.) and di-n-butylamine (32.3g. 0.25m.) added thereto. The mixture was cooled to below 40° C. and maintained below that temperature while carbon disulphide (13g.0.25m) was added. 2,6 DTN in toluene added thereto

EXAMPLE 38

2 (octanoxythiocarbonylthio) - 9 -cyano - 13 - thiabicyclo (8,2,1) tridec - 5 - ene a. Sodium cyanide (12.3g. 0.25 m.), ethanol (300 ml. 740P) and 2,9-dichloro - 13 - thia bicyclo (8,2,1) tridec-5-ene (66.3g. 0.25 m.) were mixed and the exothermic reaction allowed to proceed (35° C.) for one hour then heated for 3 hours at 75° C. After cooling water (600 ml.) was added to precipitate a product which was filtered off and dissolved in toluene.

b. Potassium hydroxide (19.8g. 0.3 m. 85% purity) was dissolved in n-octanol (200 ml.) by heating to 70° C. for ½ hour. After cooling to below 40° C. carbon disulphide (22.8g. 0.3 m.) was added over 20 minutes, a yellow precipitate being formed. The toluene solution from (a) was added over 1 hour and the mixture heated to 90° C. for 3 hours. On cooling the solution was washed three times with water (400 ml. each), toluene (400 ml.) being added to aid phase separation. The toluene solution was dried over magnesium sulphate and stripped on a rotary evaporator and then stripped under high vacuum from 70° C. at 0.1 Torr to 120° at 0.2 Torr. The residue was a viscous brown liquid which appeared to be the desired product.

Analysis of product: 13.8%S (calc. 22.6%); 0.94%Cl. (calc. 0.00%); 3.05%N (calc. 3.29%).

EXAMPLE 39

2 ethylhexyl xanthate of a polymer of 2,9-dichloro - 1 3 -thiabicyclo (8,2,1) tridec - 5 - ene Cis, trans, trans-cyclododeca - 1,5,9 - triene (324g.2m.) and sulphur dichloride (206g. 2 m.) were added simultaneously from two dropping funnels into stirred dichloromethane (1000 ml.) maintained at a temperature of 0° to 5° C. by an acetone/dry ice bath at a rate of 2 vols to 1 vol respectively. The mixture was allowed to warm to room temperature over the weekend. After heating to reflux (45° C.) for 4 hours it was cooled in a refrigerator in order to attempt recrystallisation. Since no crystals were formed the solvent was removed on a rotary evaporator. On stirring with 62°–68° C. special boiling petroleum ether, 2,9-dichloro-13-thiabicyclo (8,2,1) -tridec-5-ene (DCTT) was dissolved leaving a light brown solid polymer also insoluble in toluene which was found to contain 12.7%S (calc. 12.07%) and 23.8%Cl. (Calc. 26.8%) which figures correspond to a polymer of DCTT.

Potassium hydroxide (49.4g. 0.75 m. 85% purity) was dissolved in 2 ethyl hexanol (500 ml.) by heating to 90° C. for ½ hour, cooled to below 40° C. and carbon disulphide (57g. 0.75 m.) added over 25 minutes, toluene (100 ml.) being added to maintain fluidity. DCTT polymer (66.3g. 0.25 m.) in 2-ethyl hexanol (500 ml.) was added over 45 minutes. The solution was heated at 80°–85° C. for 4 hours, cooled, diluted with toluene (600 ml.), washed four times with water (400 mls. each) dried over magnesium sulphate and filtered. After removing the solvent on a rotary evaporator the product was stripped under high vacuum to a base temperature of 80° C. at 0.1 Torr. The product was found to contain 15.8%S (calc. 26.5%) and 1.06%Cl. (calc. 0.00%).

EXAMPLE 40

Example 39 was repeated except that the reactants were added to the dichloromethane at a temperature of 20°–30° C and then heated to 45° C for 3 hours. The mixture was then extracted with hot petroleum ether (b.pt. 62°–68° C) leaving a solid polymer found to contain 12.06%S and 28%Cl. Thereafter a subsequent reaction was carried out as described in Example 39 to yield 80g. of product.

Analysis of product: 25.1%S (calc. 26.5%); 1.71%Cl. (calc. 0.00%).

EXAMPLE 41

2,9-bis(crotyloxythiocarbonylthio)-13-thiabicyclo (8,2,1) tridec-5-ene

Example 19 was repeated except in that Intermediate B$^1$ (66.3g. 0.25 m.) was used in place of Intermediate A$^1$. Yield of product was 112g. (91.4%).

Analysis of product: 30.5%S (calc. 32.7%); 1.27%Cl. (calc. 0.00%).

EXAMPLE 42

2,6-bis(isopropoxythiocarbonylthio)-8-thiabicyclo (3,2,1) oct-3-ene 1,3,5-Cycloheptatriene (184g, 2.0 m.) and sulphur dichloride (206g. 2.0 m.) each dissolved in 250 ml. methylene dichloride were added simultaneously at equimolar rates to 500 ml. methylene dichloride at −20° C over 5 hours. The mixture was allowed to warm to room temperature overnight and the solvent stripped off on a rotary evaporator. The product was then distilled out of the residue from the rotary evaporator.

The intermediate prepared as in the preceding paragraph (114g. 0.58 m.) dissolved in 200 ml. toluene was added to 1.3 m. of potassium isopropyl xanthate and the mixture heated for 5 hours at 80° C. Further toluene was then added and the resulting solution washed with water and dried over MgSO$_4$. The toluene was then stripped off on a rotary evaporator to yield 146.4g. (64.1%) of a black liquid.

Analysis of product: 38%S (calc. 40.6%); 2.34%Cl. (calc. 0.00%).

TESTS A TO R

Certain of the compounds described in the foregoing Examples were dissolved in lubricating oil (1% solutions) and tested in the extended Petter W1 test.

The tests were carried out for 36 hours, using a Petter W1 Laboratory engine built and run according to the standard IP 176/69 procedure, except in that a sample of the oil was not taken after 16 hours. The blends under test contained an ashless dispersant, an antioxidant, a surfactant and a corrosion inhibitor.

The criterion taken was the bearing weight loss which was of the same order or lower than the bearing weight loss for zinc dialkyl dithiophosphate.

Examples 1 and 2 gave blackened bearings but when the blend was retested with 0.01% of benzotriazole the bearings had a normal colour.

The products of Examples 4 and 5 gave particularly low bearing weight losses and good colour bearings in the absence of benzotriazole.

The product of Example 3 was only soluble to the extent of 0.25% in mineral oil.

The results of these tests are given in Table 3. It can be seen that the results compare favourably with a blend containing a zinc dialkyl dithiophosphate and other ash containing additives.

In addition Copper Strip tests were carried out in accordance with IP Test Method 154/69 except in that the tests were carried out at 120° C using the test additive dissolved in 500 Solvent Neutral mineral oil in an amount sufficient to give a product sulphur level of 0.15% by weight. In this way was tested each of the products of Examples 1, 2, 4, 5, 7–13, 16, 19, 25, 28–36 and 39–41 all of which gave results of 1a or 1b.

Furthermore, the novel additives of the present invention were also found to have useful load carrying properties.

TABLE 3

| TEST | BLEND CONTAINING 1% of EXAMPLE No. | BEARING WEIGHT LOSS (mg.) | COLOUR |
|---|---|---|---|
| A | 1 | 22 | BLACK |
| B | 2 | 30 | BLACK. |
| C | 4 | 8 | STRAW. |
| D | 5 | 7 | STRAW. |
| E | 7 | 17 | STRAW. |
| F | 12 | 8.1 | BROWN TO DARK PATCHES. |
| G | 13 | 16 | LIGHT STRAW. DARK STRAW PATCHES. |
| H | 14 | 14 | STRAW. DARK STRAW PATCHES. |
| I | 15 | 14 | LIGHT STRAW, PEACOCK COLOURS. |
| J | 16 | 53.3 | DARK BROWN - BLACK LACQUER. |
| K | 17 | 22 | BROWN-PEACOCK, |
| L | 28 (1.5%) | 19 | BROWN TRACES BLACK. |
| M | 32 | 17 | STRAW-PEACOCK. |
| N | 33 | 12 | BROWN TRACES OF BLACK. |
| O | 34 | 18 | STRAW-PEACOCK |
| P | 35 | 12 | STRAW-TRACES LACQUER. |
| Q | 36 | 8 | STRAW-PEACOCK. |
| R | 39 | 20 | LIGHT STRAW-COPPER/ PEACOCK PATCHES. |

We claim:
1. compound having the formula:

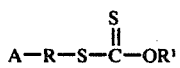      or      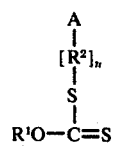

(I)                                (II)

wherein in Formula (I) R is a sulfur-bridged hydrocarbon ring derived from 1,3,5-cycloheptatriene or 1,5,9-cyclododecatriene, said sulfur-bridge being a single sulfur bridge between two non-adjacent carbon atoms of said ring forming a bicyclo compound and wherein in Formula (II) $R^2$ is a polymer comprising the residue of a plurality of n hydrocarbon rings which are derived from 1,3,5-cycloheptatriene, cyclooctatetrene, 1,3-cyclooctadiene, 1,5-cyclooctadiene, 3-alkoxy derivatives thereof and 1,5,9-cyclododecatriene, said n hydrocarbon rings being connected through a sulfur bridge, n being the degree of polymerization such that said compound is oil-soluble, $R^1$ is the same or different and is an alkyl, alkenyl or aralkyl group and A is a nucleophyllic group selected from

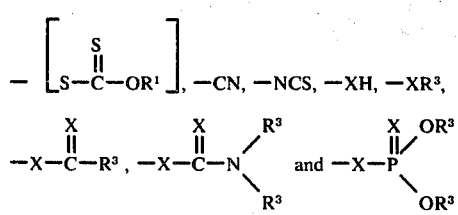

wherein $R^1$ is as above, X is oxygen or sulfur and $R^3$ is alkyl, aryl, alkaryl or aralkyl.

2. The compound of claim 1 wherein each $R^1$ is selected from the group consisting of alkyl and alkenyl groups containing from 1 to 20 carbon atoms.

3. The compound of claim 1 wherein the group A has the formula:

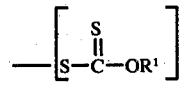

wherein $R^1$ is as defined in claim 1 and wherein the two groups $R^1$ may be the same or different.

4. The compound of claim 1 wherein the group A is selected from the group consisting of groups of the formula —CN and —NCS.

5. A compound of claim 1 having Formula (I) wherein R is derived from 1,5,9-cyclododecatriene.

6. A compound of claim 5 wherein $R^1$ is alkyl.

7. A compound of claim 6, namely 2,9-bis(butoxythiocarbonylthio)-13-thiabicyclo(8,2,1)tridec-5-ene.

8. A compound of claim 6, namely 2,9-bis(isopropoxythiocarbonylthio)-13-thiabicyclo(8,2,1)tridec-5-ene.

9. A compound of claim 6, namely 2,9-bis-(2-ethylhexanoxythiocarbonylthio)-13-thiabicyclo(8,2,1)tridec-5-ene.

10. A compound of claim 6, namely 2,9-bis-(1-methylbutoxythiocarbonylthio)-13-thiabicyclo(8,2,1)-tridec-5-ene.

11. A compound of claim 5, namely 2,9-bis(benzyloxythiocarbonylthio)-13-thiabicyclo(8,2,1)tridec-5-ene.

12. A compound of claim 1 having Formula I.

13. A lubricating composition comprising a major amount of a lubricating oil and a minor amount sufficient to improve the antioxidant properties of said oil of an oil-soluble compound of the formula

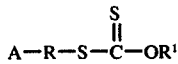      or      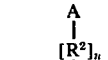

(I)                                (II)

wherein in Formula (I) R is a sulfur-bridged hydrocarbon ring containing from 6–12 carbon atoms wherein said sulfur bridge is a single sulfur bridge between nonadjacent carbon atoms of said ring forming a bicyclo compound and wherein in Formula (II) R² is a polymer comprising the residue of a plurality of n hydrocarbon rings containing from 6–12 carbon atoms, said n hydrocarbon rings being connected through a sulfur bridge, n being the degree of polymerization such that said compound is oil-soluble, each R¹ is the same or different and is an alkyl, alkenyl or aralkyl group and A is a nucleophyllic group selected from

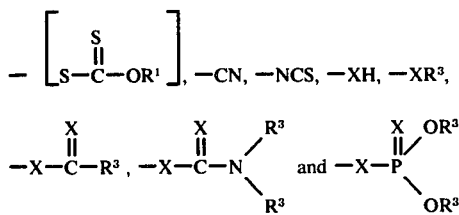

wherein R¹ is as above, X is oxygen or sulfur and R³ is alkyl, aryl, alkaryl or aralkyl.

14. The lubricating composition of claim 13 containing from 0.01 to 10% by weight of the compound of Formula (I) or (II).

15. The lubricating composition of claim 13 containing from 0.5 to 3% by weight of the compound of Formula (I) or (II).

16. A lubricating composition of claim 13 wherein R and R² are derived from an unsaturated ring compound selected from the group consisting of 1,3,5-cycloheptatriene, cyclooctatetrene, 1,3-cyclooctadiene, 1,5-cyclooctadiene, and 1,5,9-cyclododecatriene.

17. A lubricating composition of claim 13 wherein said compound has the formula

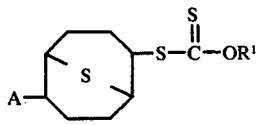

wherein R¹ and A are as defined in claim 13.

18. A lubricating composition of claim 13 wherein said compound has the formula

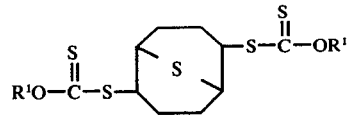

wherein R¹ is as defined in claim 13.

19. A lubricating composition of claim 18 wherein said compound is 2,6-bis(butoxythiocarbonylthio)-9-thiabicyclo-(3,3,1)nonane.

20. A lubricating composition of claim 18 wherein said compound is 2,6-bis(ethoxythiocarbonylthio)-9-thiabicyclo-(3,3,1)nonane.

21. A lubricating composition of claim 18 wherein said compound is 2,6-bis(isopropoxythiocarbonylthio)-9-thiabicyclo(3,3,1)nonane.

22. A lubricating composition of claim 18 wherein said compound is 2,6-bis(benzyloxythiocarbonylthio)-9-thiabicyclo(3,3,1)nonane.

23. A lubricating composition of claim 18 wherein said compound is 2,6-bis(2-ethylhexanoxythiocarbonylthio)-9-thiabicyclo(3,3,1)nonane.

24. A lubricating composition of claim 13 wherein said compound has the formula

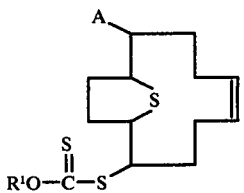

wherein R¹ and A are as defined in claim 13.

25. A lubricating composition of claim 24 wherein said compound has the formula

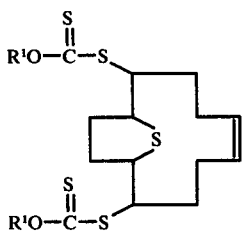

26. A lubricating composition of claim 25 wherein said compound is 2,9-bis(butoxythiocarbonylthio)-13-thiabicyclo(8,2,1)tridec-5-ene.

27. A lubricating composition of claim 13 wherein said compound has Formula I.

* * * * *

UNITED STATES PATENT AND TRADEMARK OFFICE
CERTIFICATE OF CORRECTION

PATENT NO. : 4,019,991
DATED : April 26, 1977
INVENTOR(S) : Gerald John Joseph Jayne et al It is certified that error appears in the above-identified patent and that said Letters Patent are hereby corrected as shown below:

Claim 1 - before "compound" insert -- An oil-soluble --

Signed and Sealed this nineteenth Day of July 1977

[SEAL]

Attest:

RUTH C. MASON
Attesting Officer

C. MARSHALL DANN
Commissioner of Patents and Trademarks